United States Patent [19]
Håkanson

[11] 4,084,056
[45] Apr. 11, 1978

[54] METHOD OF PRODUCING SUBSTITUTED PHENYL CARBAMATES

[75] Inventor: Christer Lennart Håkanson, Lidangsgatan, Sweden

[73] Assignee: AB Bofors, Bofors, Sweden

[21] Appl. No.: 629,430

[22] Filed: Nov. 6, 1975

[30] Foreign Application Priority Data

Nov. 11, 1974 Sweden .................................. 7414106

[51] Int. Cl.$^2$ ............................................ C07C 125/06
[52] U.S. Cl. ..................................................... 560/29
[58] Field of Search ..................................... 260/471 C

[56] References Cited
U.S. PATENT DOCUMENTS
2,860,166  11/1958  Newcomer et al. ............. 260/471 C

OTHER PUBLICATIONS

March, *Advanced Organic Chemistry: Reactions, Mechanisms and Structure*, pp. 816 and 817, McGraw-Hill, (1968).
Wallis et al., "The Hofmann Reaction", Organic Reactions, vol, III, pp. 267–306, (1962).

*Primary Examiner*—Jane S. Myers
*Attorney, Agent, or Firm*—Pollock, Vande Sande & Priddy

[57] ABSTRACT

Substituted carbamate esters are prepared by treating an aromatic amide with hypochlorite ion in the presence of water and a water-miscible solvent at a low temperature, after which the reaction mixture is mixed with a substituted phenol and allowed to react at a temperature of at least 10° C.

16 Claims, No Drawings

METHOD OF PRODUCING SUBSTITUTED PHENYL CARBAMATES

The present invention relates to a new method of producing certain substituted phenyl carbamates, which are used as herbicides. The substances in question are mentioned in the Dutch patent specification No. 6,604,363. This patent specification describes carbamates with the general formula

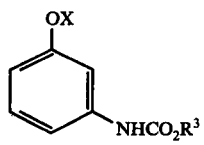

in which
X = $CONR^1R^2$ and
$R^2$ normally = H.

The substance according to the above-mentioned formula with $R^1$ = m-tolyl and $R^3$ = methyl is of particular interest. This substance, which thus has the structure

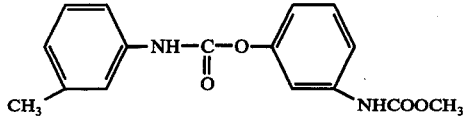

has found great use for weed killing in beet fields, and has been given the generic name of fenmedifam.

According to said Dutch specification, phenyl carbamates of this type are produced by a phenolic intermediate (X = H in the general formula above) being reacted with an aromatic isocyanate. This reaction gives a high yield, and in most cases gives an advantageous synthesizing method for production of the substituted phenyl carbamates in question. However, some of the isocyanates used in this connection are comparatively difficult to obtain. This is applicable not least to m-tolyl isocyanate, which is required for the production of fenmedifam. The m-tolyl isocyanate is normally produced via m-toluidine, starting from m-nitrotoluene which is obtained in limited quantities as a by-product when producing o- and p-nitrotoluenes. Also other aromatic isocyanates of interest for synthesis of the substituted phenyl carbamates in question can be difficult to obtain owing to similar isomer problems, and what is stated below with m-tolyl isocyanate as an example can therefore be applicable also to other isocyanates. A conceivable alternative way to m-tolyl isocyanate would be to start with m-toluic acid, available through the oxidation of m-xylene, and via m-toluamide with the aid of alkali hypochlorite solution to transform this into m-toluidine. However, this reaction, which is a so-called Hofmann reaction, leads to comparatively high costs for the m-tolyl isocyanate desired, and, accordingly, for the final product, fenmedifam. However, it is known that formation of an amine in the Hofmann reaction takes place via an intermediately formed isocyanate. This can not be isolated, but in certain cases can be trapped with the formation of products with a carbamate structure. It is thus a well-known variant of the Hofmann reaction to halogenate in the presence of an alcohol, usually methanol, in the presence of the corresponding sodium alkoxide in a stoichiometric quantity, to produce a carbamate ester of the alcohol in question. According to the U.S. Pat. No. 2,860,166, the alkoxide can be replaced by anhydrous soda.

In both cases, however, the alcohol will be subjected to the influence of chlorine (or bromine) which would make a corresponding process impossible if it were desired to use a phenolic substance in place of the alcohol. This applies not least to the derivatives of m-aminophenol, which are used for the synthesizing of fenmedifam and related phenyl carbamates, and which are extremely sensitive to the influence of halogens and hypohalites. To produce fenmedifam and related phenyl carbamates with the application of the above-mentioned principle must therefore be regarded as a very difficult problem which however, it would be of great economic interest to be able to solve.

The literature describes only one case when it has been possible for a phenolic substance to participate in a reaction of the kind sought, under the formation of the corresponding phenyl carbamate. It is G. R. Elliot, J. Chem. Soc. 121, 202-09 (1922) who carried out the reaction:

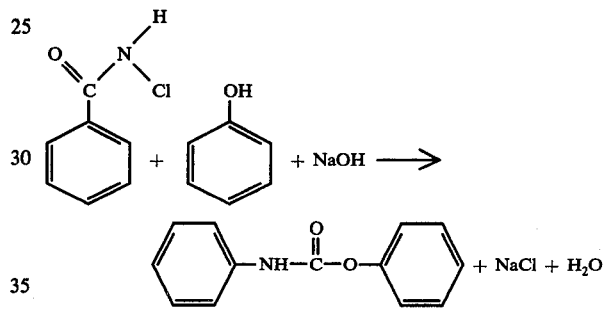

In practice, Elliot has proceeded in such a way that from benzamide he has produced and isolated benzomonochloramide, suspended this in water together with phenol, and carried out the reaction by dripping in a sodium hydroxide solution. Elliot has thus solved the problem of the sensitivity of the phenol to free chlorine and hypochlorites by first producing and isolating benzomonochloramide, and only thereafter reacting this with phenol and alkali. In an industrial application this procedure would involve a considerable extra cost, due to the increased production costs because of the extra process stage, and also due to the increased yield losses. The procedure would also involve storage and safety problems, as the chloramide has an unstable character. These problems would be still more accentuated with m-toluamide, which is required for the production of fenmedifam, the monochloramide of which is not described in the literature, and seems to be difficult to produce and isolate. Even if Elliot's method should be applicable to the production of fenmedifam, it will thus hardly be attractive from technical and economic viewpoints.

The purpose of the present invention is now to show an extremely attractive method, not previously proposed, of producing fenmedifam and similar carbamate esters from related substituted phenyl carbamates with the aid of m-toluamide or related aromatic amides, without isolating the corresponding chloramide. The method according to the invention thus offers a technically and economically realistic way of producing the carbamate esters in question, also on an industrial scale.

Generally speaking, the invention can be described as a method of producing substituted carbamate esters with the formula

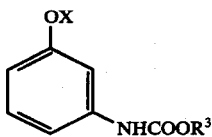

in which
X = CONR$^1$R$^2$,
R$^2$ then = H
while R$^1$ = a phenyl group or an alkyl substituted phenyl group and
R$^3$ = a lower alkyl group.

The method according to the invention is characterized in that an aromatic amide with the general formula R$^1$CONH$_2$ is treated at a low temperature with hypochlorite ion in the presence of water, after which an addition is made to the reaction mixture thus produced of a phenolic substance with the general formula

after which the synthesis is completed by the mixture being heated to a temperature of at least 10° C. Thereafter, the carbamate ester, which is normally difficult to dissolve, is separated.

It has also proved to be advantageous, in conjunction with the hypochlorite treatment of the amide, or in the second stage of the synthesis, to add a water-miscible solvent which improves the solubility of the reactants in the reaction mixture. Lower alcohols, such as methanol or ethanol, as well as glycols, have proved to be particularly suitable for this purpose.

In the procedure according to the invention, the hypochlorite necessary is moreover appropriately added in the form of an Na-hypochlorite solution of the type which is commercially available, and which is produced by absorption of chlorine in sodium hydroxide. However, it is also possible to use solutions which contain hypochlorite of other alkali or alkaline-earth metals, e.g. calcium hypochlorite.

An advantageous method of producing fenmedifam according to the invention is carried out in such a way that m-toluamide is dissolved in an appropriate quantity of methanol and is treated at a low temperature with an approximately equimolecular quantity of sodium hypochlorite solution, after which 3-methoxycarbonylamino phenol is added, also in an approximately equimolecular quantity, or in excess, after which the mixture is heated to an appropriate reaction temperature. The fenmedifam desired is formed in an exothermic reaction, and will normally precipitate successively from the solution. A variant of the invention involves that the cold solution of hypochlorite treated amide is added slowly, with stirring, to a solution of the 3-methoxycarbonylamino phenol in methanol or aqueous methanol, which is kept at an appropriate reaction temperature.

The hypochlorite treatment included in the method according to the invention is appropriately carried out at a temperature of between 0° and 10° C. The reaction with the m-alkoxycarbonylamino phenol or other phenolic substance of the type defined above can be carried out at a temperature of from 10° C or higher, but preferably not higher than approx. 65° C. It has proved to be an advantage to add the m-alkoxycarbonylamino phenol in excess, in order to suppress the formation of certain by-products. Unreacted m-alkoxycarbonylamino phenol or other phenolic substance used can thereafter be recovered from the mother liquor.

The method according to the invention will be noted from the accompanying examples of the procedure.

EXAMPLE 1

5.40 g of m-toluamide (40 mmol) was dissolved in 45 ml of methanol and 36 g of a hypochlorite solution with 8.1% active chlorine (corresponding to 40 mmol NaClO) was dripped in while stirring, the temperature, through cooling, being kept below 5° C. After 15 minutes at 0°–5°, 6.68 g (40 mmol) of 3-methoxycarbonylamino phenol was added with a spoon, and the mixture was heated carefully, while stirring. At approx. 30° a substantial exothermic reaction could be established, and within the course of approx. 10 minutes, the temperature increased to 41°. At the same time, an increasing quantity of a fine-grained precipitate was formed in the mixture, and the solution obtained a bluish-green colour. Through temporary cooling, the temperature was reduced to 39°, after which the temperature decreased by itself to room temperature within the course of 75 minutes. The reaction mixture was thereafter cooled with an ice bath to 0°–5°. After 1 hour at this temperature, the precipitated product was filtered off and washed 5 times with water, and dried. 9.85 g of raw fenmedifam was obtained, with a melting point of 137°–140°. According to thin-layer chromatography, the product contained small quantities of two impurities, which could be identified as N,N'-di-m-tolyl urea and N-m-tolyl-N'-m-toluyl urea. The yield of the raw product corresponds to 82.5% of the theoretical yield.

EXAMPLE 2

The synthesis of fenmedifam was carried out substantially according to example 1, but with the difference that after the addition of the 3-methoxycarbonylamino phenol, the reaction temperature, through cooling, was kept at 17°–20°. The reaction therefore progressed more slowly, and a reaction time of approx. 5 hours was necessary in order to complete the reaction, so that the formation of precipitate substantially ceased. A raw fenmedifam was obtained with a melting point of 137°–140° C, in a yield corresponding to 84% of the theoretical yield. According to thin-layer chromatography, the product contained the same impurities as the product from example 1.

EXAMPLE 3

The synthesis of fenmedifam was carried out substantially according to example 1, but with the difference that after the addition of the 3-methoxycarbonylamino phenol the reaction mixture was heated to 50° C. When the source of heat was removed, the temperature increased through exothermic reaction in a few minutes to 65°, and thereafter, after a few minutes more, began to decrease. After cooling and extraction as per example 1, 7.27 g of a raw product was obtained which according to thin-layer chromatography contained comparatively large quantities of impurities. The higher reaction temperature thus seems to have had an unfavourable influence.

EXAMPLE 4

The synthesis of fenmedifam was carried out substantially according to example 1, but with the difference that the 3-methoxycarbonylamino phenol was added in a quantity of 10.0 g = 60 mmol, i.e. in an excess of 50%. The reaction was carried out at approx. 30° for 65 minutes, after which the temperature was allowed to decrease to 22° and was kept there for approx. 1.5 hour. 10.15 g of a product with a melting point of 138°–141° C was obtained which according to thin-layer chromatography contained the same impurities as the product according to example 1, but in smaller quantities. The yield of raw product corresponds to 84.5% of the theoretical yield counted on the m-toluamide added.

The excess of 3-methoxycarbonylamino phenol has thus evidently had a favourable influence, by reducing the formation of byproducts.

EXAMPLE 5

The synthesis of fenmedifam was carried out substantially as per example 4, i.e. with 60 mmol of the 3-methoxycarbonylamino phenol, corresponding to a 50% excess, but before the addition of this, 3 g of a 20 percent sodium hydroxide solution = 15 mmol NaOH was added in the cold. For the rest, the reaction was carried out in the same way as in example 4. 10.16 g of a product with a melting point of 138.5°–142° C was obtained, which according to thin-layer chromatography only contained traces of impurities.

The addition of alkali corresponding to part of the phenol excess evidently had a favourable effect and further reduced the formation of by-products.

From the mother liquor, 2.82 g of practically pure 3-methoxycarbonylamino phenol was recovered. This was done by the methanol being distilled off, after which an excess of NaOH was added and undissolved neutral product was filtered off. From the filtrate, the 3-methoxycarbonylamino phenol was precipitated through acidification. The net consumption of phenol was thus 10 − 2.82 = 7.18 g, and the yield counted on this component was 78.8%.

EXAMPLE 6

The synthesis of fenmedifam was carried out with "reversed adding": 5.40 g of m-toluamide was dissolved in 22.5 ml of methanol and 36.5 g of a sodium hypochlorite solution (8.1% active $Cl_2$) was added as previously in cold. The solution obtained was put in a cooled dropping funnel, and was thereafter added in drops during 56 minutes to a solution of 6.68 g of 3-methoxycarbonylamino phenol in 22.5 ml of methanol which was kept under stirring at 34°–36° C. Thereafter the mixture was allowed to after-react for 30 minutes at 35°, and was thereafter cooled to 20°. After stirring for 1 hour at 20°, the product was filtered off and washed with water and dried. 9.41 g of a raw product with a melting point of 137°–140° was obtained, which according to thin-layer chromatography contained approximately the same quantity of impurities as the product obtained according to examples 1 and 2.

EXAMPLE 7

The synthesis of fenmedifam was carried out substantially according to example 1, but with the difference that other solvents were used instead of methanol. The results are given in the following table.

| Solvent | Yield of fenmedifam (raw product) | Melting point | Impurities according to thin-layer chromatography |
|---|---|---|---|
| Ethanol | 76% | 138–41° | ~ example 1 |
| Isopropanol | 67% | 131–7° | ". |
| Ethylene glycol | 80% | 135–9° | ". |
| Water only | 49% | 90–123° | as in example 1, and m-toluamide |

As will be noted from the above-mentioned comparative tests, water can also be used as a solvent, even if this gives a lesser yield and a rather impure product.

EXAMPLE 8

A carbamate ester analogous with fenmedifam with the formula

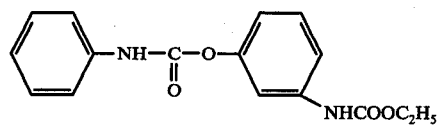

was produced, substantially according to example 1, but with the difference that instead of m-toluamide, benzamide was used, and instead of 3-methoxycarbonylamino phenol, 3-ethoxycarbonylamino phenol was used. The yield of raw carbamate ester was 80%. The melting point of the product was 117°–120° C.

EXAMPLE 9

A carbamate ester analogous with fenmedifam with the formula

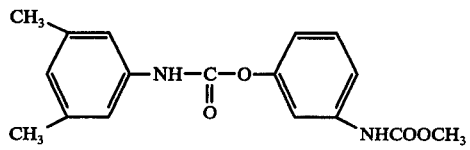

was produced substantially according to example 1, but with the difference that, instead of m-toluamide, 3,5-dimethyl benzamide was used. The yield of raw carbamate ester was 83% and the melting point was 151.5°–153.5° C.

EXAMPLE 10

The experiment made in the foregoing example was repeated with the difference that instead of Na-hypochlorite the corresponding amount of Ca-hypochlorite was added. The yield of raw carbonate ester was then 59% with a melting point of 155.0° to 156.6° C.

I claim:

1. A method of producing substituted carbamate esters with the general formula:

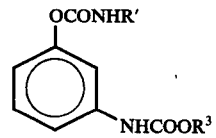

wherein R' equals phenyl group, m-tolyl group, or m-xylyl group and $R^3$ is $CH_3$ or $C_2H_5$ characterized in that an aromatic amide with the general formula $R'CONH_2$ and being benzamide, m-toluamide, or 3,5-dimethyl benzamide is treated at a temperature of 0°–10° C with an aqueous solution of alkali or alkaline earth metal hypochlorite in the presence of a water-miscible organic solvent, after which the reaction mixture thus produced is mixed with a m-alkoxycarbonylamino phenol having the formula:

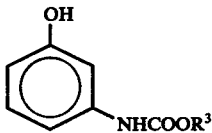

in which it is allowed to react at a temperature of 10°–65° C, after which the carbamate ester obtained is separated.

2. A method according to claim 1, characterized in that the synthesis is carried out in the presence of a lower alcohol or glycol as a solvent.

3. A method according to claim 1 characterized in that the reaction with hypochlorite is carried out at a temperature of between 0° and 5° C.

4. A method according to claim 1 characterized in that the reaction with the phenolic substance is carried out at a temperature between 15° and 40° C.

5. A method according to claim 1 characterized in that the phenolic substance is used in a quantity equimolecular to that of the aromatic amide, or in excess.

6. The method of claim 1 wherein said aromatic amide is m-toluamide.

7. The method of claim 6 wherein said phenolic substance is 3-methoxycarbonylamino phenol and wherein said carbamate ester is fenmedifam.

8. The method of claim 1 wherein said aromatic amide is benzamide.

9. The method of claim 8 wherein said phenolic substance is 3-ethoxycarbonylamino phenol.

10. The method of claim 1 wherein said $R^3$ is methyl.

11. The method of claim 1 wherein said $R^3$ is ethyl.

12. The method of claim 1 wherein said aromatic amide is 3,5-dimethyl benzamide.

13. The method of claim 12 wherein said phenolic substance is 3-methoxycarbonylamino phenol.

14. The method of claim 1 wherein said hypochlorite is sodium hypochlorite.

15. The method of claim 1 wherein said hypochlorite is calcium hypochlorite.

16. The method of claim 1 wherein said reaction mixture produced by treating said aromatic amide with said hypochlorite is mixed with said phenolic substance without isolating the corresponding chloramide produced.

* * * * *